(12) United States Patent
De Souza Russo Carbolante et al.

(10) Patent No.: US 8,969,041 B2
(45) Date of Patent: Mar. 3, 2015

(54) LARGE SCALE AND STABLE PRODUCTION OF HUMAN FVIII IN THE HUMAN CELL LINE SK-HEP-1

(75) Inventors: Elisa Maria De Souza Russo Carbolante, Ribeirao Preto (BR); Kamilla Swiech, Ribeirao Preto (BR); Dimas Tadeu Covas, Ribeirao Preto (BR); Virginia Picanco E Castro, Ribeirao Preto (BR)

(73) Assignees: Fundação Hemocentro de Ribeirão Preto, Ribeirão Preto (BR); Universidade de São Paulo, São Paulo (BR)

( * ) Notice: Subject to any disclaimer, the term of this patent is extended or adjusted under 35 U.S.C. 154(b) by 0 days.

(21) Appl. No.: 13/981,446

(22) PCT Filed: Jan. 19, 2012

(86) PCT No.: PCT/BR2012/000010
§ 371 (c)(1),
(2), (4) Date: Oct. 4, 2013

(87) PCT Pub. No.: WO2012/100312
PCT Pub. Date: Aug. 2, 2012

(65) Prior Publication Data
US 2014/0051122 A1  Feb. 20, 2014

(30) Foreign Application Priority Data
Jan. 24, 2011 (BR) .............................. PI 1105317-8

(51) Int. Cl.
*C12P 21/06* (2006.01)
*C07K 14/755* (2006.01)

(52) U.S. Cl.
CPC ........... *C07K 14/755* (2013.01); *C12N 2531/00* (2013.01)
USPC ...................................................... 435/69.1

(58) Field of Classification Search
USPC ...................................................... 435/69.1
See application file for complete search history.

(56) References Cited

U.S. PATENT DOCUMENTS

| | | | |
|---|---|---|---|
| 5,362,641 A | 11/1994 | Fuks et al. | |
| 5,422,260 A | 6/1995 | Kaufman et al. | |
| 5,693,499 A | 12/1997 | Yonemura et al. | |
| 5,789,203 A | 8/1998 | Chapman et al. | |
| 5,994,136 A | 11/1999 | Naldini et al. | |
| 6,114,146 A | 9/2000 | Herlitschka | |
| 6,228,620 B1 | 5/2001 | Chapman et al. | |
| 6,271,025 B1 | 8/2001 | Negrier et al. | |
| 6,346,513 B1 | 2/2002 | Van Ooyen et al. | |
| 6,919,311 B2* | 7/2005 | Lenting et al. ............... | 530/383 |
| 7,247,707 B2 | 7/2007 | Besman et al. | |
| 2002/0042130 A1 | 4/2002 | Hebbel et al. | |
| 2002/0165177 A1 | 11/2002 | Negrier et al. | |
| 2010/0172891 A1* | 7/2010 | Fontes et al. ................ | 424/94.5 |

FOREIGN PATENT DOCUMENTS

| | | |
|---|---|---|
| EP | 0 123 945 A1 | 11/1984 |
| EP | 1 136 553 A1 | 9/2001 |
| EP | 1 233 064 A1 | 8/2002 |
| EP | 0 813 597 B1 | 10/2006 |
| WO | 86/06101 | 10/1986 |
| WO | 92/16557 | 10/1992 |
| WO | 93/15105 | 8/1993 |
| WO | 96/15140 | 5/1996 |
| WO | 96/15150 | 5/1996 |
| WO | 96/40883 | 12/1996 |
| WO | 0170968 A2 | 9/2001 |
| WO | 2004/092355 A1 | 10/2004 |

OTHER PUBLICATIONS

Resumo de Tese de doutorado de Virginia Picanco defendida em Jan. 1, 2006 Intitulada: Clonagem e Expressao do FVIII de Coagulacao Humano, disponivel na biblioteca central USP Ribeirao Preto.

Boedeker BDG 2001 "Production processes of licensed precombinant factor VIII Preparations" Semin Thromb Hemost. 27(4): 385-94.

Herlitschka, Sabine et al., "High expression of a B-domain deleted factor VIII gene in a human hepatic cell line", J Biotechnol. 61, 1998, pp. 165-173.

Picanco et al., "Recombinant expresion of coagulant factor VIII in hepatic and non-hepatic cell lines stably transduced with 3rd generation lentiviral vectors comprising minimal FVIII promoter", Cytotherapy 9(8), 2007, pp. 785-794.

Russo-Carbolante et al., "Integration pattern of HIV-1 based lentiviral vector carrying recombinant coagulation factor VIII in SK-Hep and 293T cells", Biotechnol Lett (2011) 33:23-31 Epub Sep. 2, 2010.

Wood, William I. et al., "Expression of active human factor VIII from recombinant DNA clones", Nature, vol. 312, Nov. 22, 1984, pp. 330-337.

Zelechowska, Maria G. et al. "Ultrastructural localization of factor VIII procoagulant antigen in human liver hepatocytes", Nature, vol. 317, Oct. 24, 1985, pp. 729-730.

Toole, John J. et al., "Molecular cloning of a cDNA encoding human antihaemophilic factor", Nature, vol. 312, Nov. 22, 1984, pp. 342-347.

(Continued)

*Primary Examiner* — Maryam Monshipouri
(74) *Attorney, Agent, or Firm* — Carter, DeLuca, Farrell & Schmidt, LLP

(57) ABSTRACT

The present invention refers to: 1) the method for the production of recombinant FVIII in human Sk-Hep-1 cells, comprising von Willebrand Factor (vWF) and 2) the population of human cells transduced with a vector encoding the clotting protein (FVIII). The technical object of the present patent application is intended for the cultivation of human cells in suspension and in adhesion and isolation of the culture medium containing the desired protein. The object of the invention is to provide a safer product (free of potential human viruses), that is cheaper and more stable, by means of a method that provides sufficient amounts and on industrial scale to meet the National demand.

8 Claims, 3 Drawing Sheets

(56) References Cited

OTHER PUBLICATIONS

Gitschier, Jane et al., "Characterization of the human factor VIII gene", Nature, vol. 312, Nov. 22, 1984, pp. 326-330.
Do, Hung et al., "Expression of Factor VIII by Murine Liver Sinusoidal Endothelial Cells", J. Biol. Chem., vol. 274, No. 28, Jul. 9, 1999, pp. 19587-19592.
Wion, Karen L. et al., "Distribution of factor VIII mRNA and antigen in human liver and other tissues", Nature, vol. 317, Oct. 24, 1985, pp. 726-729.
Hollestelle, Martine J. et al., "Tissue Distribution of Factor VIII Gene Expression in Vivo—A Closer Look", Thromb Haemost, vol. 86, 2001, pp. 855-861.
Heffelfinger, Sue C. et al., "SK HEP-1: A Human Cell Line of Endothelial Origin", in Vitro Cell. Dev. Biol., vol. 28A, Feb. 1992. pp. 136-142.

* cited by examiner

LARGE SCALE AND STABLE PRODUCTION OF HUMAN FVIII IN THE HUMAN CELL LINE SK-HEP-1

CROSS REFERENCE TO RELATED APPLICATIONS

This application is a U.S. National Phase Application of International Patent Application No. PCT/BR2012/000010, filed Jan. 19, 2012, which claims priority from Brazilian Patent Application No. PI 1105317-8 filed on Jan. 24, 2011, the disclosures of each of which are hereby incorporated by reference herein in their entirety.

OBJECT OF THE PATENT

The present invention relates to the method for the production of recombinant FVIII in human Sk-Hep-1 cells, comprising von Willebrand Factor (vWF).

The technical object of the present patent application is intended for the cultivation of human cells in suspension and in adhesion and isolation of the culture medium containing the desired protein. The invention further relates to the population of human cells transduced with a vector encoding the clotting protein (FVIII). These cells can be used in the method of production of the protein.

The present invention is then connected with the pharmaceutical industry.

STATE OF THE ART

Hemophilia A patients are treated by means of intravenous infusion of plasma-derived or recombinant FVIII (Mannucci and Giangrande, 2000).

Currently in Brazil, due to the high costs of recombinant plasma, treatment of hemophiliacs is made using factors VIII purified from plasma of normal individuals, which strategy has disadvantages such as risks for viral infections and high demand for plasma from normal donors. Despite being a somewhat effective treatment for hemophilic patients, this is not ideal.

Production of recombinant factor VIII (FVIIIr) in mammal cells represents a safer and more effective alternative for the treatment of individuals with hemophilia A.

In the Brazilian market, each international unit (IU) of plasma-derived factor VIII is sold at an average price of US$ 0.80. Each hemophilic patient uses an average of 30,000 UI per year, which represents US$ 17,000.00/patient/year. Based on these numbers, it is estimated that the country spends about US$ 140,000,000.00 per year in the treatment of these patients. This is an extremely expensive treatment and patients do not receive a suitable prophylactic treatment since there is not enough product on the market and due to contamination risks. Lack of prophylaxis decreases life quality and expectancy of these patients.

All recombinant FVIII available on the market is produced transiently, that is, by plasmid vectors that do not integrate into the genome of cells and murine cells are used for production.

Using non-human cell lines for producing recombinant factor VIII has certain disadvantages. Currently, the main limitation in the production of recombinant FVIII is the low yield of FVIII, which is two orders of magnitude lower than that of other proteins.

The only recombinant FVIII products currently available on the market are under the leadership of three companies (Bayer, Baxter, Wyeth). They are KOGENATE and KOGENATE FS by Bayer, RECOMBINATE by Baxter and REFACTO by Wyeth/Genetics Institut. The recombinant protein is produced in CHO (Chinese Hamster Ovary) or BHK (Baby Hamster Kidney) cells, which are transfected with the full-length or B domain-deleted FVIII. All these recombinant products have similar biological activity than plasma-derived FVIII. Safer formulations have been developed over the years, but these industries use conventional plasmid vectors which provide low expression and the recombinant protein is produced in murine CHO and BHK cell lines, which show different glycosylation patterns thereby yielding a product having high probability for causing an immune reaction in patients.

U.S. Pat. No. 5,362,641 (Heparanase derived from human Sk-Hep-1 cell line) uses Sk-Hep-1 cell line (human liver endothelial cell) to produce recombinant Heparanase.

Patent (WO/2004/092355) EXPRESSION OF PROTEINS IN CORD BLOOD-DERIVED ENDOTHELIAL CELLS and US Patent 2002/0042130 A1 and Lin et al. (2002) describe the production of FVIII in human endothelial cells that can be used in gene therapy protocols.

Patents U.S. Pat. No. 6,228,620, U.S. Pat. No. 5,789,203 and U.S. Pat. No. 5,693,499 describe the co-expression of DNA encoding FVIII light and heavy chains. These embodiments can also be used in accordance with the present invention.

Part of the B-domain of the therapeutic protein used in the present invention is deleted (or removed), which does not take part in coagulant activity of FVIII. Removal of part of the B-domain of FVIII is a known method and patents U.S. Pat. No. 6,346,513, WO 86/06101, WO 92/16557, and EP 0 123 945 describe deletions in sequences encoding FVIII B-domain. In this method, as discussed in the present patent application, cPPT-C(FVIIIDB) vector is used, which is obtained as described in patent IGWS (WO/2004/092355).

Patents EP 1 233 064, US 2002/0165177 and U.S. Pat. No. 6,271,025 disclose the insertion of introns into the cDNA that codes for factor VIII. U.S. Pat. No. 5,422,260 discloses point mutations in FVIII DNA coding sequence.

Factor VIIIr (recombinant) has at least one of the following mutations (EP 1 136 553 A1): —valine at position 162 is substituted with another neutral amino acid residue; —serine at position 2011, is substituted with another hydrophilic amino acid; —valine at position 2223 is substituted with an acidic amino acid. At the B-domain, between positions arginine 740 and glutamic acid 1640, there is a substitution with an arginine-rich "linker" oligopeptide containing 10 to 25 amino acids, preferably 14-20 amino acids. These positions refer to the amino acid sequence of mature human factor VIII (Toole et al. 1984, 312 Nature (5992): 342-7; Wood et al. 1984, 312 Nature (5992): 330-7; Gitschier et al. 1984, 312 Nature (5992): 326-30).

DNA encoding FVIIIDB (FVIII cDNA with part of the B-domain removed) is part of the vector that is used to transduce human cells.

OBJECTS OF THE INVENTION AND SOLUTION PROPOSED TO SOLVE THE CITED PROBLEMS

The present invention uses a human cell line that can be grown in monolayer and/or suspension.

The object of the invention is to provide a safer product (free of potential human viruses), that is cheaper, more stable and produced in sufficient amounts and on an industrial scale to meet the National demand.

The technical improvement observed herein over what already exists is the possibility of obtaining FVIII in a safer manner, since it derives from human cells which are less likely to trigger immune reactions, and on a large scale due to production in suspension. Techniques existing so far do not contemplate how to obtain FVIIIr stably produced in human cells and in suspension.

Under physiological conditions, synthesis of FVIII takes place primarily in hepatocytes and liver sinusoidal endothelial cells (Wion et al., 1985; Zelechowska et al., 1985; Do et al., 1999; Hollestelle et al., 2001). Base on this information, a human liver endothelial cell (Sk-Hep-1) is used to produce recombinant FVIII.

Sk-Hep-1 cell used herein is characterized in that it expresses the von Willebrand Factor (FvW), which is released into the culture medium (Heffelfinger S C et al., 1992). When cells express FVIII, the FvW:FVIII mole ratio in the supernatant may range from 1:1 to 100:1.

FvW stabilizes FVIII. Thus, the production of recombinant FVIII is carried out in a human cell line, Sk-Hep-1.

The blood coagulation FVIII recombinant protein of the present invention has part of the B-domain deleted (FVIIIDB), is produced at high levels in adhesion (monolayers) and suspension cultivation strategies, has good stability, being suitably used in the treatment of hemophilia A.

DEFINITIONS

Recombinant FVIII—is an artificial form of a protein, in this case clotting FVIII, which is created by combining two or more sequences. Recombinant FVIII is created by means of introduction of part of the cDNA human FVIII into a viral DNA, in this case a lentivirus.

B-domain—part of the molecule structure of factor VIII that is not essential for clotting activity thereof.

cDNA—complementary DNA. Molecule that is synthesized by molecular biology techniques using as a template a RNA molecule extracted from the parent producing organism. The molecule is complementary to the RNA.

GFP—Green fluorescent protein. The gene encoding green fluorescent protein is introduced into the cell together with the FVIII coding gene. When produced by cells it acts as an indicator of the production of the molecule of interest (FVIII) and helps in the selection of these producing cells due to the production of green color.

Sk-Hep-1—immortalized human endothelial cell line

FVIIIDB—FVIII recombinant Molecule without part of B-domain

Vector—DNA molecule to which another DNA fragment can bind. A vector can, for example, carry therein an antibiotic resistance gene, replicate autonomously and have a sequence recognizable by enzymes that cut this molecule (endonuclease).

Viral envelope—protein envelope that coats and surrounds all the virus forming material. Each type of virus has different proteins forming this envelope, which provides unique features to each virus.

Plasmid—plasmids are DNA circular molecules capable of reproducing independently from the chromosomal DNA.

Plasmid DNA—same definition as before

Sk-Hep-FVIIIDB—Sk-Hep-1 cell modified by viral transduction and that starts producing factor VIII molecule pVSV-G—one of the types of viral envelope. Derived from vesicular stomatitis virus. It is used with an envelope for the lentivirus employed herein. Therefore, the HIV viral genetic material is surrounded by an envelope from another virus and is designated pseudotyped (envelope from another virus). This method increases safety to prevent the assembly of a HIV virus.

FACS—Fluorescence Activated Cell Sorting. Process for selecting cells in accordance with its fluorescence.

Cytodex 3—beads of a biologically inert matrix used as microcarriers for growing cells in suspension. It consists of a thin layer of collagen chemically coupled to a dextran matrix.

Cultispher G—macroporous gelatin beads used as microcarriers for growing cells that remain anchored on its surface.

Transduction—the same as viral infection. Process by which viruses produced are placed together with cells in culture. Owing to the intrinsic characteristics of lentiviruses, the viral genetic material fuses or integrates with the genomic material of the cell, thereby modifying its DNA and causing the cell to transform into a FVIII producer.

PBS—Phosphate buffered solution. Aqueous saline solution of 0.9% NaCl buffered with phosphate at pH 7.4.

BRIEF DESCRIPTION OF THE FIGURES

The following description will enable the understanding of the invention as a whole and of each detail thereof

2A) Comparison between FVIIIr and FVIIIdp activity profiles over time. FVIIIr shows higher levels of biological activity and is more stable than FVIIIdp.

B) Survival curve after bleeding induced in mice that received FVIIIr (all of them survived), FVIIIdp (all of them survived, and control mice (did not receive FVIII and died until 30 hours after bleeding started).

Figure 3:
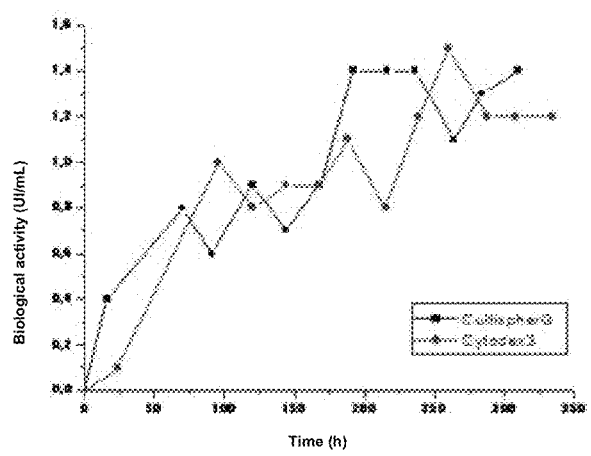

FIG. 3 illustrates escalation of the generated Sk-Hep-FVIIIBD cell line and analysis of recombinant FVIII production in suspension. The use of two microcarriers is shown to be effective in culturing Sk-Hep-FVIIIDB, which produces up to 1.2 to 1.4 units of FVIIIr/mL.

Figure 4:
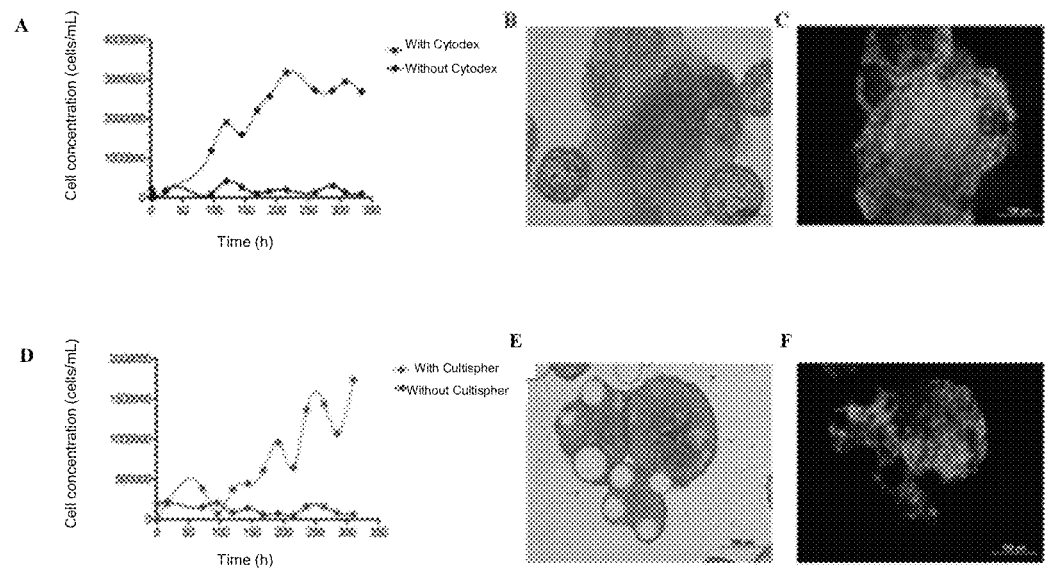

FIGS. 4A and 4D show, respectively, the kinetics of growth of Sk-Hep FVIIIGFP-CMVdelB cell on Cytodex 3 and Cultispher-G microcarriers in a spinner flask. FIGS. 4B, 4C, 4E and 4F show the formation of cells-microcarriers aggregates in the culture with Cytodex 3 (4B and 4C) and Cultispher-G (4E and 4F).

Figure 5:
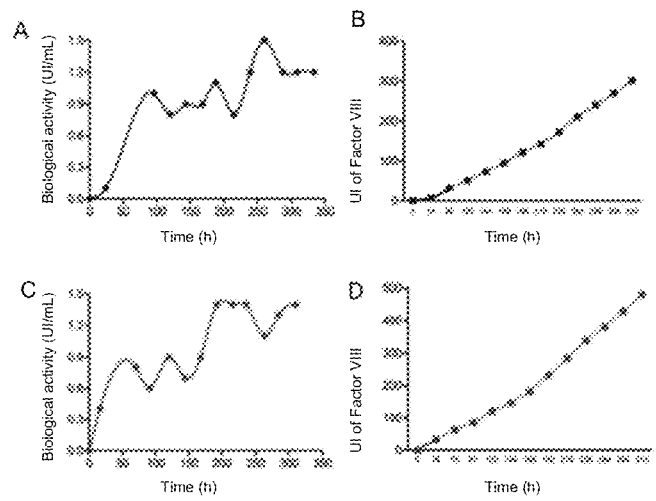

FIG. 5 illustrates the kinetics of FVIIIr production in cultures using Cytodex 3 (A and B) and Cultispher-G (C and D) microcarriers. (A and C) Biological activity and (B and D) Cumulative production over cultivation.

DESCRIPTION OF THE INVENTION

Method

The method for obtaining recombinant FVIII without part of the B-domain comprises the following steps:

1—Producing FVIIIDB-containing virus particles
2—Using the virus particles to infect Sk-Hep-1 cell line
3—Selecting GFP (Green Fluorescent protein used to select producing cells)-positive cells
4—Cultivation in suspension
5—Recovering FVIIIr produced by Sk-Hep-1 cells Step 1 of the Method: Production of FVIIIDB-Containing Virus Particles Step 1 consists of producing FVIIIDB-containing virus particles and is carried out by means of the lipofectamine method (Lipofectamine 2000, Gibco).

By using lipofectamine, virus particles are obtained, which have FVIII cDNA with the B-domain partially deleted (FVIIIDB) and the GFP protein. Virus particles are used to insert the gene of interest (in this case FVIIIDB-GFP) into Sk-Hep-1 cells.

Three plasmid vectors are used: a lentiviral vector containing the gene of interest, the plasmid responsible for generating the viral capsid (p8.91) and a plasmid to form the viral envelope (pVSV-G).

Figure 1:
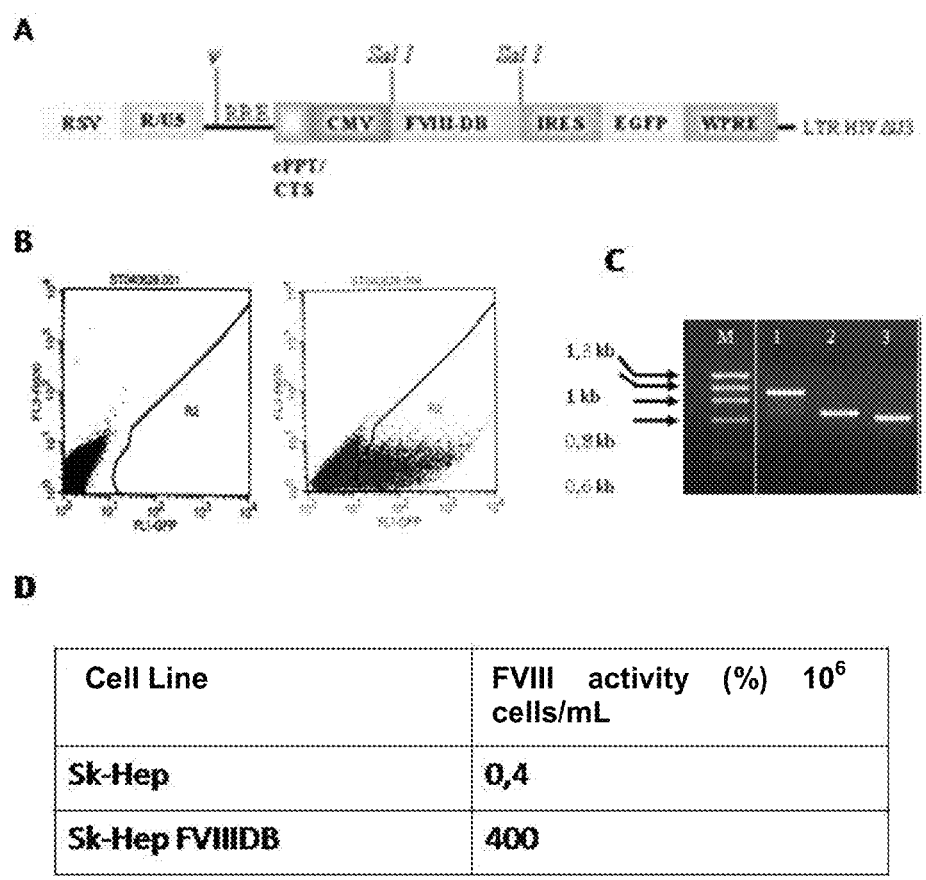
FIG. 1A is the schematic representation of the expression lentiviral vector.
FIG. 1B shows flow cytometry, GFP-positive cells selected and expanded.
FIG. 1C refers to the use of RT-PCR to detect expression of FVIIIr light and heavy chains expressed by the SK-Hep-FVIIIDB population.
FIG. 1D demonstrates the biological activity of recombinant FVIII.

The vector containing the gene of interest includes a promoter operably linked to a DNA sequence encoding coagulation factor FVIII. The vector is viral, may be a retroviral vector, more preferably, a lentiviral vector. The lentiviral vector is a HIV-1-derived vector. In addition to HIV-1, lentiviral vectors from HIV-2, simian immunodeficiency virus, equine infectious anaemia virus, feline immunodeficiency virus (FIV) can be used. The schematic representation of the vector is shown in FIG. 1A.

Viruses or virus particles are produced in a mammal cell line (HEK-293) using the 3 plasmid DNAs cited above, which method has already been described by U.S. Pat. No. 5,994,136. Cells produce the viruses which are secreted into the culture medium, which is collected, filtered and stored at −80° C. until use.

Viruses produced by these cells are designated lentiviral vectors or virus particles and are collected and used in step 2.

Step 2 of the Method: Use of Virus Particles to Infect Sk-Hep-1 Cell Line

Next (step 2), human Sk-Hep-1 cell is transduced with FVIIIDB-containing virus particles.

Viruses produced in the previous step (lentiviral vectors) are used in the transduction procedure when the genetic material of interest (human FVIIIr cDNA) is carried to host cell genome, thus resulting in stable integration into the cell genome. After integration of the viral genome material with the DNA of the cell, transcription of the transgene, and consequently, synthesis of recombinant protein, begins. Usually, the recombinant protein can be detected a few hours after transduction.

Step 3: Selection of GFP-Positive Cells

The lentiviral construct used in the present patent has GFP cDNA, such that transduction efficiency is measured by flow cytometry (FACS). Fluorescent cells detected by the flow cytometer indicate that infection and integration took place and since they express GFP, they also express FVIII.

After selection by FACS, evaluation of the recombinant protein production level is made by conventional RT-PCR and by an activity, chromogenic assay.

Step 4: Cultivation in Suspension

Expansion of Sk-Hep-FVIIIDB cell may be carried out in spinner bootles with microcarriers.

The cell line produced in accordance with the present invention should be previously expanded in bottles up to the concentration of $1 \times 10^5$ cells/mL and added to the previously hydrated, sterilized and balanced microcarriers in serum-containing growth medium at 37° C.

Step 5: Recovery of Recombinant FVIII Produced by Sk-Hep-FVIIIDB Cells

In this step recombinant FVIII is isolated from Sk-Hep-FVIIIDB cells.

The quantity of the purified protein during and after the purification procedure may be monitored (or measured) by ELISA and by coagulation assays.

The composition obtained by this method for the production of FVIII is subjected to a viral inactivation treatment and purification to remove chemical substances.

Example of Obtainment

The invention can be obtained by the previously cited steps, which are explained below:

Step 1 of the Method: Production of FVIIIDB-Containing Virus Particles

Step 1 consists of producing FVIIIDB-containing virus particles and is carried out by means of the lipofectamine method (Lipofectamine 2000, Gibco).

Production of virus particles using lipofectamine é a method where 3 DNAs are used, namely 10 ug of lentiviral vector, 6.5 ug of 8.91 vector (capsid) and 3.5 ug of VSVG vector (envelope). Prior to adding the DNAs, the culture medium of HEK-293 cells is replaced. 7 ml of DMEM containing 10% fetal bovine serum (FBS) are added.

In a 15 ml tube, pipette 8.91 and VSVG DNAs into 1.5 ml of serum-free DMEM medium. In another tube, mix 1.5 ml of serum-free DMEM medium with 60 ul of Lipofectamine. Leave both tubes at ambient temperature for 5 minutes.

Next, mix the 2 tubes and incubate for 20 minutes at room temperature. Add the resulting 3 ml to the plate with cells and incubate at 37° C. 5% $CO_2$. After 6 hours, replace the medium on the plates (7 ml of DMEM medium with 10% FBS) and incubate for at least 48 hours at 37° C. 5% $CO_2$. The culture supernatant containing the viruses produced by the cells is collected after 48 hours, filtered and fractionated into 1 ml aliquots.

Step 2 of the Method: Use of Virus Particles to Infect Sk-Hep-1 Cell Line

Transduction may be carried out in adherent cells as well as in cultures in suspension. Several transduction techniques using both viral and non-viral vectors have been optimized to cell culture in suspension.

Transductions are carried out in 24-well plates. Twenty-four hours prior to transduction 2 to $5 \times 10^4$ Sk-Hep-1 cells are seeded in DMEM medium with 10% FBS for transduction to take place during the exponential phase of cell growth. To each well the previously produced and collected virus is added with no dilution. Cells are centrifuged (90 minutes, 1250×g, 32° C.), incubated for 15 to 18 hours in a moist $CO_2$ incubator, washed with PBS and expanded with the appropriate medium.

Step 3: Selection of GFP-Positive Cells

Transduction efficiency is measured by flow cytometry (FACS).

For the FACS procedure, cells are trypsinized with trypsin/EDTA, washed with the appropriate buffer (1% fetal bovine serum/0.1% sodium azide in PBS) and 1% formaldehyde in PBS is added. Non-transduced cells, which do not express GFP, are used as a negative control, that is, Sk-Hep-1 cells which have not received any viruses are also passed through the flow cytometer to evaluate basal fluorescence of cells. Basal fluorescence is compared with that of transduced cells Identification and purification of the cell population harboring the FVIIIDB-containing lentiviral vector is shown in FIG. 1B.

GFP-positive cells selected by flow cytometry can be re-cultured in DMEM medium with 10% FBS at a temperature of 37° C. and 5% CO2.

After selection by FACS, evaluation of the recombinant protein production level is made by conventional RT-PCR and by an activity, chromogenic assay. The chromogenic assay is made by ELISA or luminescence. The chromogenic assay used was Immuno Chrom (Immuno GmbH, Germany).

Step 4: Cultivation in Suspension

Expansion of Sk-Hep-FVIIIDB cell may be carried out in spinner booties with microcarriers. Microcarrier cell culture allows for cultivation of anchorage-dependent cell lines at an industrial scale to meet the commercial demand. In this type of culture, cell grows adhered to the surface of small beads or inside the pores of macroporous particles which are suspended in a culture medium. The system allows for control of culture parameters (pH, dissolved oxygen concentration, temperature, among others), reduces the need for high amounts of culture medium, reduces labor and contamination risks.

First, microcarriers should be hydrated and sterilized, as is known by the skilled person.

Microcarriers can be, for instance, Cytodex 3 (GE Healthcare) and Cultispher-G (Percell Biolytica).

Re-hydration of microcarriers Cultispher-G was performed in calcium- and magnesium-free PBS (50 ml/g dry Cultispher-G) for at least one hour, more preferably 2 to 3 hours, at room temperature. Without removing PBS, microcarriers were sterilized (121° C., 15 min, 15 psi).

Re-hydration of microcarriers Cytodex 3 was performed in calcium- and magnesium-free PBS (50 ml/g dry Cytodex 3) for 3 to 6 hours at room temperature. Sterilisation was performed as explained above for microcarriers Cultispher-G.

Sk-Hep FVIIIGFP-CMVdelB cells can be cultured in culture bottles, such as spinner flasks, in incubators at 37° C. and 5% CO2. The cell line obtained in the present invention should be first expanded in bottles up to the concentration of $5 \times 10^4$ cells/mL up to $2 \times 10^5$ cells/mL, preferably about $1 \times 10^5$ cells/mL, and then added to previously hydrated, sterilized and balanced microcarriers in a serum-containing growth medium at 37° C. and up to a concentration of about 3.0 g/L Cytodex 3 and about 1.0 g/L Cultispher-G.

Culture was initiated with ⅓ the final volume and intermittent stirring (stirring for 2 minutes at 20-50 rpm, more preferably at 30-40 rpm, followed by about 30 minutes with no stirring) for the first 3 hours for better adhesion of cells to the microcarrier. After this period of time, DMEM culture medium containing 10% FBS was added to make the final volume and stirring was kept constant at 30 to 40 rpm, more preferably, at 40 rpm. Replacements of 50% of the volume of the culture medium were performed when the pH fell to the range of 6.5 to 7.2 after sedimentation of cell-containing microcarriers.

Samples were collected daily for monitoring cell density, viability and production of recombinant factor VIII.

Results of production escalation and analysis of FVIII activity during cultivation are shown in FIG. 3.

FIGS. 4A and 4D, in turn, show cell growth using Cytodex 3 and Cultispher-G. Sk-Hep FVIIIGFP-CMVdelB cell was capable of growing on the two microcarriers tested for a period of more than 300 hours of cultivation, achieving a maximal cell density of $3.17 \times 10^6$ cel/mL for Cytodex 3 (FIG. 4A) and $1.74 \times 10^6$ cel/mL for the Cultispher-G microcarrier (FIG. 4D).

FIG. 5 shows data of FIG. 3 separately. It can be noted that the production profile of recombinant factor VIII was similar in both cultures (FIGS. 5A and B). The average production of rFVIII was $0.9 \pm 0.4$ IU/mL on Cytodex 3 microcarrier and $1.0 \pm 0.4$ IU/mL on Cultispher-G microcarrier. Total cumulative production was 300 UI in the culture with Cytodex 3 (334 hours) and 480 UI in the culture with Cultispher-G (310 hours) (FIGS. 5C and D). Even after 200 hours of culture, Sk-Hep FVIIIGFP-CMVdelB cell was capable of producing higher levels at 1.0 UI/mL.

Step 5: Recovery of Recombinant FVIII Produced by Sk-Hep-FVIIIDB

In this step recombinant FVIII is isolated from –Hep-FVIIIDB cells. Suitable purification methods include, but are not limited to, immunoaffinity chromatography, ion exchange chromatography and so on, and combinations thereof. Execution purification protocols for human blood coagulation factors are disclosed in patent documents: WO 93/15105, EP 0 813 597, WO 96/40883, 96/15140/50 and U.S. Pat. No. 7,247,707 B2. They can be tailored to the necessary demands to isolate recombinant factors VIII and IX.

The quantity of the purified protein during and after the purification procedure may be monitored (or measured) by ELISA and by coagulation assays. The composition obtained by this method of producing FVIII is subjected to a viral inactivation treatment that includes heat treatment (either dry or in liquid state, with or without the addition of chemical substances, including protease inhibitors). After viral inactivation a further purification step may be required to remove chemicals. Patent document WO 93/15105 describes a technique to isolate factor VIII from blood plasma by ion exchange chromatography in high purity.

Selection by Flow Cytometry

The lentiviral construct used in the present invention has GFP cDNA, such that transduction efficiency was measured by flow cytometry (FACS). For the FACS procedure, cells were trypsinized with trypsin/EDTA, washed with FACS buffer (1% FBS/0.1% sodium azide in PBS) and 1% formaldehyde in PBS is added. Measurement and selection has been carried out in a FACScan apparatus using Becton Dickinson CellQuest software. Non-transduced cells, which do not express GFP.

Flow cytometry analysis has shown a population prior to selection containing 8.4% GFP-positive cells and after selection the population obtained was 73% GFP-positive (FIG. 1A).

Conventional RT cDNA molecules were synthesized from 4 μg of total RNA by incubating 50 ng/μL oligo FVIII or β-actin, 10 mM dNTPs, in a volume of 10 μL at 65° C. for 5 minutes, followed by cooling on ice for 2 minutes. Thereafter, a mixture of 2 μL of RT-Buffer 10×, 4 μL of 25 mM MgCl, 2 μL of 0.1 M DTT and 1 μL of ribonuclease inhibitor was added to the mixture, thus yielding a final volume of 19 μL. The reaction was incubated at 25° C. for 2 minutes, 1 μL of SuperScript II RT (50 units) was added to each sample followed by 25° C. for 10 minutes. The reaction was then incubated at 42° C. for 50 minutes and denatured at 70° C. for 15 minutes and put on ice, with the addition of 1 μL of RNAse H and incubation at 37° C. for 20 minutes. Samples incubated with no reverse transcriptase enzyme have been prepared as a control. After reverse transcription, 1 μL of cDNA was used in PCR amplification with specific oligonucleotides for FVIII and β-actin.

Amplification of regions of recombinant FVIII is demonstrated in FIG. 1B.

Quantification of FVIII Activity by a Chromogenic Assay

The chromogenic assay measures FVIII activity via production of factor Xa, rather than by the clotting time, as in the TTPA assay. Two reagents (A: phospholipids and albumin; B: FIX, FX, Ca2+, albumin and thrombin) were added to the samples. Factor VIII present in the samples acts as a co-factor together with FIX, Ca2+ and phospholipids to transform FX into FXa. FXa breaks the p-nitroaniline substrate down, thereby yielding an yellow color whose concentration is measured at 405 nm. The chromogenic assay used was Immuno Chrom (Immuno GmbH, Germany), according to the manufacturer's instructions. The assay was carried out in 96-well microplates. For each microplate, a standard curve of defined dilutions of human plasma was made. The minimum detection level of the assay is for samples showing ≥1% activity.

The activity of recombinant FVIII was found to be 4 UI/mL/10E6 cells. It can be verified by RT-PCR (reverse transcription polymerase chain reaction—reverse transcriptase reaction followed by a polymerase chain reaction) used to detect expression of FVIIIr light and heavy chains expressed by the SK-Hep-FVIIIDB population (FIG. 1C). It is noted that the cell line obtained according to the present invention produces 4 times more FVIII than the amount of FVIII in human plasma.

Test in an Animal Model—Functionality of Recombinant Protein

To test the in vivo functionality of the recombinant protein obtained according to the present invention, the following experiment was performed.

Figure 2:
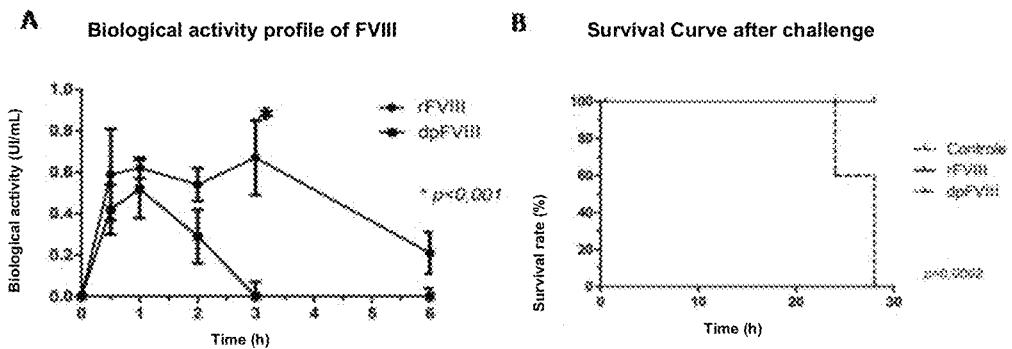
FIGS. 2A and B show the test for determining efficacy of recombinant FVIII in hemophilia A mice.

Functionality of the recombinant protein was tested in hemophilia A mice and compared with FVIIIdp efficiency (derived from plasma). Five mice were given 1 UI of recombinant FVIII or FVIIIdp and biological activity was monitored for 30 minutes, 1 hour, 2 hours, 3 hours and 6 hours after FVIII infusion. The results are depicted in FIG. 2A.

Hemophilia A mice were anesthetized and were given 50 UI of FVIIIDB/Kg, then bleeding was provoked by cutting 3 mm of the tail. The survival curve is shown in FIG. 2B. All animals that were given FVIIIDB survived, showing effectiveness of the FVIIIDB obtained according to the present invention in correcting hemophilia A.

The invention claimed is:

1. A method for the production of blood coagulation factor VIII (FVIII) protein, comprising:
   obtaining FVIIIDB-containing virus particles which comprise GFP protein;
   transducing human Sk-Hep-1 cells with the FVIIIDB-containing virus particles to form Sk-HEP-FVIIIDB cells;
   culturing the SK-HEP-FVIIIDB cells in suspension using microcarriers under appropriate conditions;
   purifying the FVIII protein from cell culture media; and
   subjecting the FVIII protein to heat treatment for viral inactivation, wherein the culturing step produces up to 1.2 to 1.4 units of FVIIIr/ml.

2. The method of claim 1, wherein the purification step includes isolating the FVIII protein from the Sk-Hep-FVIIIDB cells.

3. The method of claim 1, wherein the FVIIIDB-containing virus particles are formed in a mammal cell line (HEK-293) using at least three plasmid vectors.

4. The method of claim 3, wherein at least one of the plasmid vectors is a lentiviral vector.

5. The method of claim 4, wherein the lentiviral vector is selected from the group consisting of HIV-1 derived vector, HIV-2 derived vector, simian immunodeficiency virus, equine infectious anaemia virus, feline immunodeficiency virus, and combinations thereof.

6. The method of claim 1, wherein, after the transduction step, the method further comprises identifying transduced Sk-Hep-1 cells and non-transduced Sk-Hep-1 cells based on the presence of the GFP protein.

7. The method of claim 2, wherein activity of the purified FVIII protein is about 4 UI/mL/10E6 cells.

8. The method of claim 2, wherein the method produces four (4) times more FVIII protein than an amount of FVIII normally found protein in human plasma.

* * * * *